(12) United States Patent
Heffels et al.

(10) Patent No.: US 6,535,283 B1
(45) Date of Patent: Mar. 18, 2003

(54) APPARATUS FOR SPECTROSCOPIC ANALYSIS OF A FLUID MEDIUM BY ATTENUATED REFLECTION

(75) Inventors: Camiel Heffels, Gernsheim (DE); Thomas Beuermann, Mannheim (DE); Matthias Rädle, Weisenheim (DE); Benno Sens, Neustadt (DE); Alfred Rennig, Böchingen (DE); Jürgen Ettmüller, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/453,490

(22) Filed: Dec. 3, 1999

(30) Foreign Application Priority Data

Dec. 8, 1998 (DE) ......................... 198 56 591

(51) Int. Cl.[7] .................................. G01J 3/00
(52) U.S. Cl. ..................... 356/300; 250/341.8
(58) Field of Search .................. 356/300, 51, 128, 356/440, 442, 446, 301, 302, 303, 309, 136; 250/338, 341.8, 347, 339.1

(56) References Cited

U.S. PATENT DOCUMENTS

| 4,829,186 | A | * | 5/1989 | McLachlan et al. | 250/373 |
| 5,426,713 | A | * | 6/1995 | VonBargen | 385/15 |
| 5,610,708 | A | * | 3/1997 | Anderson et al. | 356/128 |
| 5,625,459 | A | * | 4/1997 | Driver | 356/446 |
| 6,118,520 | A | * | 9/2000 | Harner | 356/73 |
| 6,128,091 | A | * | 10/2000 | Uchida et al. | 356/432 |
| 6,205,272 | B1 | * | 3/2001 | O'Rourke et al. | 385/33 |

FOREIGN PATENT DOCUMENTS

| DE | 12 69 816 | 12/1975 |
| EP | 0 206 433 | 12/1986 |
| EP | 0 221 011 | 5/1987 |

OTHER PUBLICATIONS

N.J. Harrick, Journal of the Optical Society of America, vol. 55, No. 7, pps. 851–857, "Electric Field Strengths at Totally Reflecting Interfaces", Jul., 1965.

M. R. Querry, Journal of the Optical Society of America, vol. 59, pps. 876–877, "Direct Solution of the Generalized Fresnel Reflectance Equations", Jul., 1969.

J. Fahrenfort, et al., Spectrochimica Acta, vol. 18, pps. 103–1116, "On the Determination of Optical Constants in the Infrared by Attenuated Total Reflection", 1962.

* cited by examiner

Primary Examiner—Frank G. Font
Assistant Examiner—Layla Lauchman
(74) Attorney, Agent, or Firm—Oblon, Spivak, McClelland, Maier & Neustadt, P.C.

(57) ABSTRACT

The disclosure is a probelike apparatus (16) for spectroscopic analysis of a fluid medium (19) by attenuated reflection. Two light beams from a light source (11) impinge upon the boundary (18) between a prism (17) and the medium (19) to be analyzed and the intensities of the light beams reflected at the boundary are measured in a detector unit (22). The two light beams differ in their angle of incidence on the boundary and/or in their polarization state. Measurement is preferably carried out under total reflection.

22 Claims, 4 Drawing Sheets

APPARATUS FOR SPECTROSCOPIC ANALYSIS OF A FLUID MEDIUM BY ATTENUATED REFLECTION

BACKGROUND OF THE INVENTION

1. Field of the Invention

The present invention relates to an apparatus for spectroscopic analysis of a fluid medium by attenuated reflection, preferably by internal reflection spectroscopy and especially by attenuated total reflection (ATR).

The invention relates particularly to a novel apparatus for continuous reaction monitoring, for example for in-situ or on-line reaction monitoring in the chemical industry.

2. Discussion of the Background

Optical analytical methods such as transmission spectroscopy have hitherto only been used to a very limited extent for the continuous monitoring of reactions on an industrial scale. Owing to the high concentrations arising in manufacturing processes, coupled with large extinction coefficients in some cases, the pathlengths of the measuring cells would have to be on the order of 1 micrometer to obtain useful absorption spectra. It is therefore necessary to take samples and to prepare them, for example by dilution, for a measurement in the laboratory. But this process of sample preparation may alter the chemical equilibrium of the sample, so that lab results are not necessarily applicable to conditions in the reactor.

It is known that these transmission spectroscopy problems can be avoided by conducting measurements utilizing the well known optical phenomenon of the total reflection of light. When light traveling within a first medium having a refractive index $n_1$ impinges upon a boundary between that medium and a medium of lower refractive index $n_2$, it is totally reflected, i.e., does not pass into the second medium, when the sine of the angle of incidence $\theta$ is greater than the ratio of the refractive index of the second medium to the refractive index of the first medium ($\sin \theta > n_2/n_1$). Although the reflection is referred to as total, the light, owing to its wave nature, does penetrate a short distance into the second medium. The depth of penetration is usually on the order of the wavelength of the light. If the light does not interact with the second medium, then the coefficient of reflection, i.e., the ratio of the intensity of the reflected light to the intensity of the incident light, is 1 and the reflection is indeed "total". If, however, a portion of the light which penetrates into the second medium (the so-called evanescent wave) is absorbed or scattered therein, this results in a reduced coefficient of reflection and the effect is known as "attenuated total reflection". Computing the negative decadic logarithm of the degree of transmission, i.e., the reciprocal of the coefficient of reflection R, gives the quantity of decadic extinction customary in absorption spectroscopy, which is usually known as the absorbance A:

$$A = -\log\left(\frac{1}{R}\right)$$

Methods and apparatuses utilizing this simple relation so as to carry out absorption measurements by attenuated total reflection in chemical analysis are known. European Patent Application EP-A-0 206 433, for example, describes an ATR probe for measuring the concentration of a light absorbing substance in a fluid medium. An optical fiber is used to couple light at a certain angle into an ATR prism where it is totally reflected one or more times at a boundary between the prism and the medium to be analyzed. The reflected light emerges from the prism via a second optical fiber which transmits the light to two detectors via a bandpass filter each. One of the filters has a transmission wavelength at which no absorption is expected in the medium, and is used as reference signal, while the other filter has a transmission wavelength at which absorption does take place in the medium. The concentration measurement is effected by comparing the measured intensity ratio with calibration measurements carried out on solutions of known concentrations.

European Patent Application EP-A-0 221 011 discloses a method for analyzing dye solutions by attenuated total reflection. This reference also describes a probelike apparatus for spectroscopic analysis of a fluid medium by attenuated total reflection. It comprises a prism which is mounted in a holder and which shares with the medium to be analyzed one or more boundaries at which incident light is totally reflected and then transmitted to a detection unit. The reference proposes various applications in the chemical industry, especially in dye manufacture.

However, existing processes and apparatuses have disadvantages. For example, absorption spectra obtainable according to the prior art depend not only on the absorption coefficient of the sample, but also on its refractive index, which may vary, for example owing to temperature changes.

It is also well known that absorption spectra obtained via ATR measurements exhibit a bathochromic shift, i.e., a shift to longer wavelengths, compared with transmission spectra. This shift is due to the fact that the refractive index n of the absorbing medium to be analyzed and hence the depth of penetration of the evanescent light is wavelength-dependent (Harrick, J. Opt. Soc. Am. 55, 851–857, 1965). Accordingly, a single determination of the coefficient of reflection of the totally reflected light is not sufficient for accurate sample analysis.

From German Patent 12 69 816 C2 a device for measuring attenuated total reflection is known comprising a goniometer which allows for changing the angle of incidence of a single light beam. The time consuming mechanical adjustment of the angle of incidence does not allow for continuously monitoring chemical reactions.

SUMMARY OF THE INVENTION

It is an object of the present invention to provide an apparatus for continuous spectroscopic analysis of fluid mediums which permits precise and economical in-line monitoring of industrial reaction processes. The apparatus of the invention shall be useful in particular in an aggressive environment at comparatively high temperatures.

We have found that this object is achieved by the apparatus of the accompanying main claim. The present invention accordingly provides an apparatus for spectroscopic analysis of a fluid medium by attenuated reflection, comprising first means for directing a first light beam onto a boundary or interface of the medium to be analyzed and means for measuring the intensity of the first light beam reflected at the boundary. The apparatus according to the invention further includes second means for directing a second light beam onto a boundary of the medium to be analyzed and means for measuring the intensity of the second reflected light beam, the first and second light beams differing in their respective polarization state and/or in their angle of incidence upon the boundary.Said first and second light beams are directed substantially simultaneously onto said boundary.

By "angle of incidence" is means herein, as is customary in optics, the angle between the incident light beam and the perpendicular to the boundary. By "light" is meant in the present context not just visible light. The apparatus of the invention is also useful in the IR region or in the UV region. The preferred wavelength region for using the method of the invention ranges from 200 nm to 20,000 nm.

The invention is predicated on the concept that the reflection of a light beam at the boundary between two dielectric media is describable by the classic Fresnel equations. It is found that the coefficient of reflection is dependent, inter alia, on the angle of incidence of the light and on its polarization state.

The apparatus of the invention makes it possible to carry out two different, mutually independent reflection measurements, so that it is possible to determine decoupled dispersion spectra $n(\lambda)$ and absorption spectra $k(\lambda)$ of the medium. These spectra, unlike those produced by conventional ATR spectroscopy, are not bathochromically shifted, since the influence of the different depths of penetration of the evanescent light on the measured reflection spectra can be corrected.

Unlike the apparatuses known from EP-A-0 206 433 and EP-A-0 221 011, the apparatus of the invention is not restricted to angles of incidence which are larger than the limiting angle of total reflection. This is because Fresnel's equations show that, for smaller angles too, the coefficient of reflection is dependent not only on the refractive index $n(\lambda)$ but also on the absorption coefficient $k(\lambda)$ of the medium to be analyzed, i.e., when absorption occurs in the medium it is not just the beam passing through the medium which is attenuated but also the beam reflected at the boundary.

In a first embodiment of the apparatus of the invention, the angle of incidence of the first light beam on the boundary is $\theta_1$ and the angle of incidence of the second light beam on the boundary is $\theta_2$, which differs from $\theta_1$. Both the beams are reflected at the boundary and conducted to suitable detection means.

This apparatus makes it possible, for example, to measure the total intensity in the case of beams reflected at these two angles. The wavelength-dependent coefficients of reflection for the two angles can be used, as will be shown hereinafter, to assign numerical values to $n(\lambda)$ and $k(\lambda)$. There is no need for polarizers, so that the apparatus is relatively inexpensive to manufacture and can be used especially under harsh conditions in chemical reaction monitoring, for example at high temperatures and pressures and in an aggressive environment. Since it is only total intensities which are still measured in a polarization-independent way, there is no need either for costly polarization-preserving optical fibers. The apparatus of the invention provides an exact determination of the refractive index n and of the absorption coefficient k, which depends only on the accuracies of the reflection measurements and of the calculation and therefore permits in particular the exact description of an absorption spectrum or a dispersion curve of the medium to be analyzed. Simple optical components can be used, especially relatively inexpensive multimode optical fibers.

"Total intensity" for the purposes of the present invention is to be understood as meaning a measurement of the polarization-independent intensity of the reflected light.

The angles of incidence of the two light beams preferably differ by an amount in the range from 5 to 20°, particularly preferably by about 10°.

In one variant, the angle $\theta_1$ is larger than the limiting angle of total reflection while the angle $\theta_2$ is smaller than the limiting angle of total reflection. In this case, the intensity of the first reflected beam is more dependent on $k(\lambda)$, while the intensity of the second reflected beam is more dependent on $n(\lambda)$.

In a particularly preferred variant, however, both the angles $\theta_1$ and $\theta_2$ are larger than the limiting angle of total reflection. This represents the case of an ATR probe, but the ATR probe of the invention differs from prior art probes in that it utilizes two measuring beams.

The apparatus of the invention is preferably constructed as an elongate probe comprising a cylindrical protective housing at whose free end face is disposed a prism having at least one face which is wettable by the medium to be analyzed and which forms the boundary for the reflection of the two light beams. The prism/medium boundary is a clearly defined, planar surface, as is preferred for the impingement of light on an air/medium boundary.

However, there may also be a separate boundary with the medium for each light beam. These two boundaries may be realized by one prism or else by two prisms.

Advantageously the prism is mounted replaceably in the probe. For each measuring problem it is then possible to select an appropriate prism. Different prism geometries make it possible, for example, to use different angles of incidence. Different prism materials permit a selection with regard to transmission properties and refractive index.

The cylindrical protective housing is advantageously formed of chemically resistant metallic or ceramic materials. In this way it is possible to realize dip probes up to 2.5 m in length for use on an industrial production scale. In a particularly preferred embodiment, the prism is forced by suitable elastic means, for example compression springs, against sealing means surrounding an opening in the end face of the cylindrical housing. The compression springs serve to compensate the longitudinal expansion of the probe in the event of an increase in the temperature and maintain a good seal with regard to the prism, since the necessary contact pressure is ensured even at high temperatures. The probe of the invention can therefore also be used in the case of process temperatures of 200° C. or more or in the case of wildly fluctuating temperatures. An example of a useful sealing means is a gasket in the shape of a circular ring. This design makes it possible to fabricate dip probes more than two meters in length with just one seal. Such comparatively long probes are preferably installed in customary dip tubes, i.e., gas inlet tubes, so as to obtain good mechanical stability in stirred vessels, for example.

The prism is preferably a crystal which, for measurements in the UV to near IR region, is composed of materials which have a high refractive index and are substantially chemically resistant, such as quartz glass, sapphire or diamond, zirconium oxide or zirconia (doped zirconium oxide). For infrared measurements it is preferable to employ semiconductor crystals, for example ZnSe crystals. Preferably the entire optical device is fixedly mounted, eliminating the need for reconfiguration and adjustment.

For an ATR prism composed of quartz and refractive indices in the range from 1.2 to 1.7 for the mediums to be analyzed, the angles of incidence are preferably in the range from 55 to 60° for the first beam and in the range from 65 to 70° for the second beam. Preferably the prism has an essentially frustoconical shape and comprises a light entry and exit face parallel to the boundary, a first pair of mirror-symmetrically opposite side faces which form an angle of $\theta_1/2$ with the normal to the boundary, and a second pair of mutually opposite mirror-symmetrical side faces which form an angle of $\theta_2/2$ with the normal to the boundary.

In this embodiment of the apparatus according to the invention, the two light beams pass essentially vertically through the horizontal light entry and exit face into the prism, are reflected at one of the side faces of the first or second side-face pair and impinge at an angle of $\theta_1$ or $\theta_2$, respectively, upon the boundary, where they are diverted to the other side face of each pair. There, they are vertically reflected upward and emerge from the prism with a parallel offset relative to the incident beam. To avoid light loss, the reflection at the side faces is total as well. In one variant, the prism is arranged in such a way that one or both of the side faces of a pair are likewise wetted by the medium to be analyzed, so that each light beam undergoes two or three "attenuated" reflections. In a particularly preferred variant, however, only the lower boundary is wetted by the medium. In this case, the prism holder will be constructed in such a way that no absorption of the evanescent light takes place at the side faces in order that the measurement of the medium may not be distorted.

Advantageously the first side-face pair is twisted by 90° around a normal to the boundary relative to the second side-face pair, resulting in a particularly compact apparatus.

In a second embodiment of the apparatus according to the invention, the optical path of the first light beam includes pre-boundary a polarizer for perpendicularly polarized light and/or post-boundary an analyzer for perpendicularly polarized light and the optical path of the second light beam includes pre-boundary a polarizer for parallel-polarized light and/or post-boundary an analyzer for parallel-polarized light. As light is reflected at the boundary, a certain amount of depolarization may occur. It is therefore preferable in this case to use both a polarizer and an analyzer for each light beam.

What is measured in this embodiment is not, as in the prior art, the total intensity of the reflected light, but, separately, the intensities of the two polarization directions of the light parallel to the plane of incidence $I_p$ and perpendicular to the plane of incidence $I_s$. For this case, Fresnel's equations have been analytically solved for the desired parameters of the medium, i.e., for the refractive index n and the absorption coefficient k (Querry, "Direct Solution of Generalized Fresnel Reflectance Equations", J. Opt. Soc. America, 59 (1969), 876–877). The angles of incidence of the two beams may be identical. In principle it would also be possible here to use just one light beam and to switch the polarizers and analyzers or, for example in the case of the use of polarizing films, turn them by 90° between two successive measurements.

This embodiment of the probe according to the invention is advantageous in that it makes use of the known analytical solutions to enable the desired spectra to be calculated directly and rapidly from the measurements. However, the use of polarizers or analyzers is mandatory.

In a third embodiment of the apparatus according to the invention, the optical path of the first and second light beams include pre-boundary polarizers for perpendicularly polarized light and/or post-boundary analyzers for perpendicularly polarized light. The light beams impinge upon the boundary at different angles of incidence. Again, it is preferable to use both polarizers and analyzers.

For this case of a reflection measurement with perpendicularly polarized light and two different angles of incidence, an iteration method has been described for solving the Fresnel equations (Fahrenfort and Visser in Spectrochim. Acta 18, 1103–1116 (1962)).

In the probe of the invention, the light is advantageously not focused on the boundary; instead the light should impinge upon the boundary in as parallel a state as possible, for exact compliance with the chosen angle of incidence. It is therefore particularly advantageous to provide first optical fibers for passing the incident light beams onto the boundary and second optical fibers for directing the light beams reflected at the boundary to the means for measuring the light intensities, in which case collimating means are disposed between the light exit faces of the first optical fibers and the boundary, and between the boundary and the light entry faces of the second optical fibers, respectively for coupling the light beams in and out, respectively.

In an embodiment of the apparatus according to the invention, which for cost reasons is particularly preferred for use as a monitoring probe in chemical production, the measurement is carried out polarization-independently at two different angles. This is because high quality polarizers capable of withstanding temperatures of above 200° C. are very costly and therefore uneconomical for many monitoring duties. Also, the use of reflection probes in process monitoring has gained popularity in recent years especially because the use of optical fibers made it possible to have the probe head with the prism and the actual measuring unit (spectrometer, sensor and microprocessor) far apart. Polarization-dependent measurements would therefore also require the use of costly polarization-preserving single mode fibers.

A measuring process using a probe according to the invention will now be more particularly described by way of example. A polarization-independent measurement is carried out at two different angles of incidence. Total reflection shall occur at both angles of incidence, i.e., an ATR probe is used.

A first light beam is in a conventional manner allowed to impinge under total reflection upon the boundary between the prism and the medium to be analyzed, at a first angle of incidence $\theta_1$. The total intensity $I_1$ of the totally reflected light beam is measured at a certain wavelength l. According to the invention, in addition, a second light beam is allowed to impinge under total reflection upon the boundary at an angle of incidence $\theta_2$, which differs from the first angle of incidence $\theta_1$, and the total intensity $I_2$ of the totally reflected second light beam is measured. The two measurements are then used to calculated the absorption coefficient $k(\lambda)$ and/or the refractive index $n(\lambda)$.

When used for monitoring industrial chemical processes, each beam is usually totally reflected at the boundary only once. In thin, weakly absorbing mediums, however, multiple total reflection at the boundary may also be provided for in one variant. A measuring arrangement suitable for this purpose—albeit for measurements at only one angle of incidence—is described in EP-A-0 206 433, for example.

The accuracy of wavelength measurement depends on the particular purpose. For spectroscopic studies, for example, the need for a higher resolution will require the use of a grating spectrograph positioned in front of a diode array or other polarization-independent detection means. If, for example, there is only interest in monitoring the formation of a certain reaction component, then there is no need to record a spectrum and instead, for example, suitable bandpass filters can be used to isolate a characteristic wavelength range in which the absorption characteristics of the properties are expected to change as the reaction proceeds.

The two light beams are preferably measured simultaneously or substantially simultaneously, for example by providing a separate detection array for each reflected light beam.

Such a setup can also be used to simultaneously measure a plurality of wavelengths, i.e., to record a larger region of the spectrum. Useful sensitive diode arrays are known and typically have 256, 512 or 1024 diodes (the MMS or MCS arrays from Zeiss, for example). The signals from the diodes are amplified and processed by a microprocessor. The choice of diode arrays can be influenced by numerous factors, for example the desired resolution, the time available for on-line evaluation, the computing power, the accuracy required for measurement and computation, etc.

To calculate the constants n and k of interest, the present example utilizes polarization-independent detectors to measure the total intensity of the reflected light. The coefficient of reflection for a given angle of incidence is then made up as per $$R_\theta(n, k) = \frac{R_s}{2}\left(1 + \frac{R_p}{R_s}\right)$$

from the perpendicularly polarized fraction $R_s$ and the parallel-polarized fraction $R_p$. According to Fresnel's formulae, the coefficient of reflection is also dependent on the angle of incidence $\theta$, so that different coefficients of reflection $R_{\theta 1}$ and $R_{\theta 2}$ result for the two light beams. An analytical solution of Fresnel's formulae for n and k is not possible for this case. The actual values of n and k have to satisfy the following two relations simultaneously:

$$R_{\theta 1}(n,k) = R_1$$

and $$R_{\theta 2}(n,k) = R_2$$

i.e., the theoretical coefficient of reflection $R_{\theta 1}$ has to be equal to the measured coefficient of reflection $R_1$ of the first light beam for n and k. A corresponding relation has to be satisfied for the second light beam for the same n and k.

To solve this nonlinear system of equations, the invention proposes forming a function F(n,k) of the following structure:

$$F(n,k) = (R_{\theta 1}(n,k) - R_1)^2 + (R_{\theta 2}(n,k) - R_2)^2$$

i.e., the sum of the advantageously squared differences of the two theoretical coefficients of reflection $R_\theta$ and of the respective measured coefficient of reflection R, and numerically minimizing F. The squaring of the difference terms leads to a continuous function F, facilitating minimization. $R_\theta$ is obtained from Fresnel's formulae by the following relation:

$$R_\theta(n,k) = \frac{1}{2}\frac{(a-\cos\theta)^2+b^2}{(a+\cos\theta)^2+b^2}\left(1 + \frac{(a-\sin\theta\tan\theta)^2+b^2}{(a+\sin\theta\tan\theta)^2+b^2}\right)$$

where $a - ib = \sqrt{m^2 - \sin^2\theta}$ $$m = \frac{(n-ik)}{n_0}$$

where m is the complex refractive index of the medium and $n_0$ is the refractive index of the optical element, i.e., of the prism, for example. Algorithms for minimizing a nonlinear function having two parameters are known. Particular preference is given to using a Broyden-Flatcher-Goldfarb-Shanno minimization algorithm (unconstrained quasi-Newton minimization) as described for example in the standard work "Numerical Recipes in C" and implemented in the MATLAB Optimization Toolbox, The Math Works Inc.

The MATLAB Toolbox optimization technique requires a computing time of about 19 seconds on a 133 MHz Pentium computer (PENTIUM® is a registered trademark of Intel) for 256 spectral points and an estimated error of $10^{-4}$ in the determination of n and k.

The evaluation time can be reduced, depending on requirements. For example, it is possible to use faster processors or to use a plurality of processors in a parallel array.

Advantageously the coefficients of reflection $R_1$ and $R_2$ following r1 and r2 total reflections (usually: r1=r2=1) are determined from the measured intensities $I_1$ and $I_2$ according to the following relation:

$$R_{1,2}(\lambda) = \left(\frac{I_{1,2}(\lambda)}{I_{ref}}\right)^{\frac{1}{r1,2}}$$

The reference intensity $I_{ref}$ corresponds essentially to the intensity $I_0$ of the light source used. Since a light source may be subject to intensity fluctuations in the course of a measurement, it is advantageous to measure the reference intensity continuously as well. This may be accomplished, for example, by incorporating in the spectrometer a third diode array for wavelength-dependent measurement of the intensity $I_0$. For particularly accurate measurements, the intensity $I_0$ will be additionally weighted using the transmission curve of the entire optical system, advantageously by also taking account of the grating function of the spectrometer. This is because the transmission curve of the measuring system will generally also show a certain degree of wavelength dependence, which will be particularly noticeable when the region of the spectrum measured is relatively large. The corresponding transmission curve $I_{trans}(\lambda)$ is determined once for a given setup and can then be stored for the evaluation of later measurements.

The apparatus of the invention is particularly useful for applications in the chemical industry. Typical examples are continuous concentration measurements or absorption-spectroscopic studies of chromophoric systems in dye synthesis, in the manufacture of paints and generally in the processing of highly concentrated organic substances. The method of the invention provides for the first time the possibility of precise in-situ concentration measurements of substances which absorb strongly in the UV region, such as hydrosulfite, benzaldehyde or styrene, by preparing linear calibration curves.

The reflection measurements which can be performed using the probe of the invention are insensitive to solid particles more than a few micrometers in diameter, which is particularly advantageous in the case of measurements where there is a danger that comparatively large particles will distort the measurement. On the other hand, fine pigment dispersions in paints or printing inks can be reliably investigated.

BRIEF DESCRIPTION OF THE DRAWINGS

An illustrative embodiment of the present invention will now be more particularly described with reference to the accompanying drawings, where.

DESCRIPTION OF THE PREFERRED EMBODIMENTS

Figure 1:
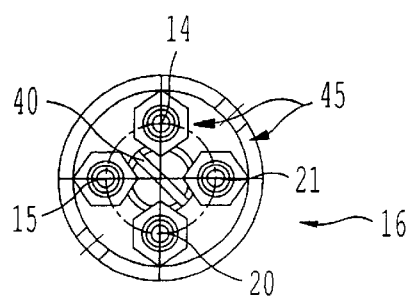
FIG. 1 shows a schematic overview of an attenuated total reflection (ATR) measuring setup according to the invention.
Figure 3:
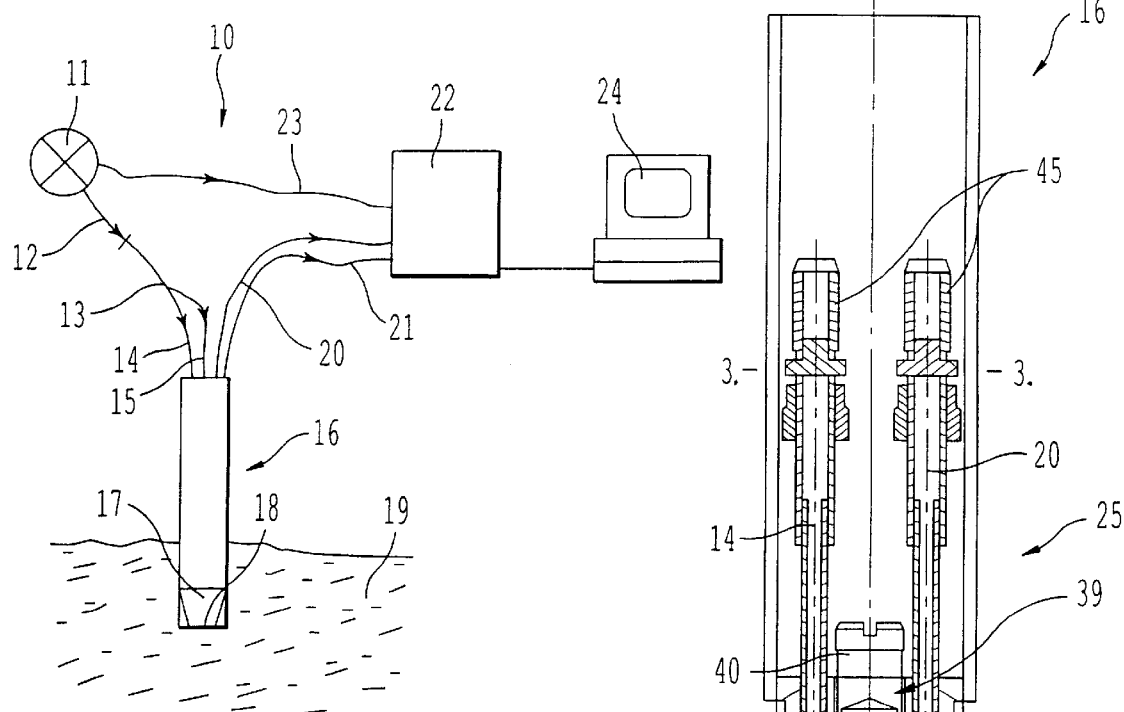
FIG. 3 shows a section alone the line III—III of the probe in FIG. 2.
Figure 3:
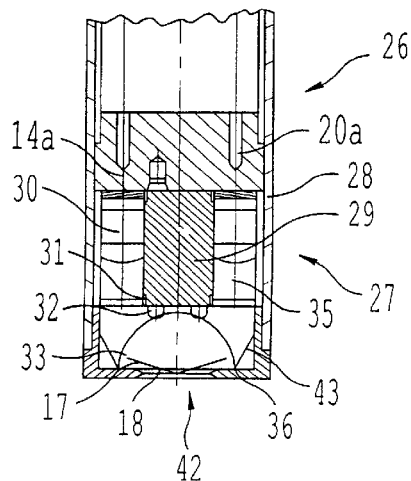
Figure 2:
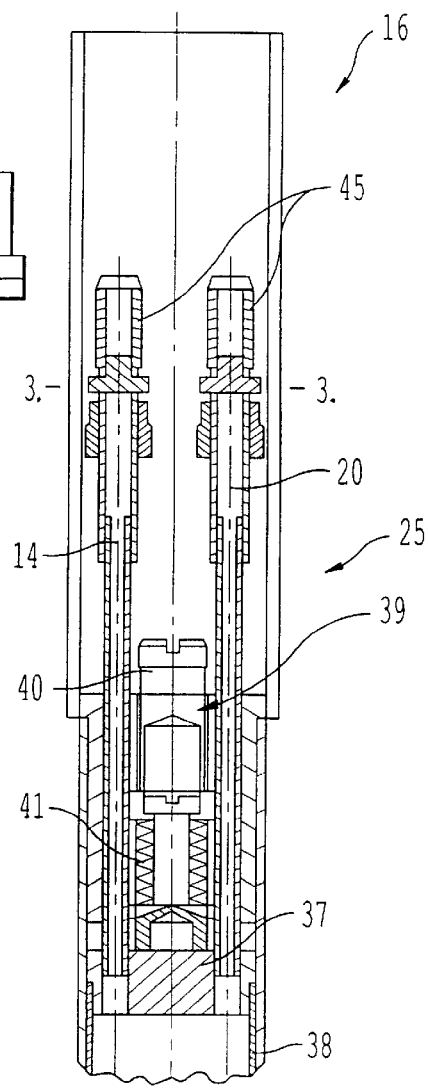
FIG. 2 shows an ATR probe according to the present invention in the form of a dip probe.

Referring now to FIGS. 1 to 3, it is initially seen that FIG. 1 is a schematic diagram of an apparatus for spectroscopic analysis of fluid mediums according to the invention. It shows the specific case of an ATR probe where measurement is carried out polarization-independently at two different angles of incidence.

Light from a lamp 11 is coupled into a first optical fiber 12 which, in a Y-branch 13, diverges into two optical fibers 14, 15 for the incident first and second light beams, respectively. The optical fibers are guided into a probe 16 which, in the illustrated example, is configured as a dip probe and is equipped at one end with an ATR prism 17, at whose boundary 18 with the medium 19 the two light beams are totally reflected at different angles. The ATR probe 16 is illustrated in FIGS. 1 and 2 in section along the plane of incidence of the first light beam. The plane of incidence of the second beam is essentially perpendicular to the plane of incidence of the first beam.

The reflected beams pass via optical fibers 20, 21 to a spectrometer 22 which includes two diode arrays (not depicted) which record the spectra produced at a grating (likewise not depicted). A further optical fiber 23 leads directly from the lamp 11 to the spectrometer 12, where the spectral intensity distribution of the light source 11 is recorded via a third diode array (likewise not depicted). The amplified signals from the diode arrays in the present example are read out via a multiplexer and processed by a personal computer 24.

FIG. 2 illustrates a sectional view of the upper part 25 and the lower part 26 of a preferred embodiment of the ATR probe 16. The probe head 27, which dips into the medium 19 to be analyzed, has a protective housing 28 which accommodates a fiber carrier 29. This fiber carrier receives the ends 14a, 20a of the four optical fibers 14, 15, 20, 21. The depicted section shows the optical fiber 14 for the first beam which impinges with an angle of incidence of 60°. At the point of exit 14a from the optical fiber 14 is disposed a first collimating means 30, which bundles the light into a broadened, parallel light beam whose diameter is limited by an aperture 31. The light beam passes via a light entry and exit face 32 (compare FIG. 5) into the ATR prism 17 and is deflected at a side face 33 in the direction of boundary 18, where the beam is totally reflected. After a further deflection at the face 43, the beam reemerges from the prism 17 by the light entry and exit face 32 and is coupled by a second collimating means 35 into the optical fiber 20. A gasket 36 is situated between the housing 28 and the prism 17's steplike sealing base which surrounds the boundary 18 and is visible in FIGS. 5 and 6 in particular.

In the case of variants of the probe according to the invention which are based on measurements with polarized light, suitable polarizers and analyzers could be provided in the region of the collimating means 30 and 35, respectively, for example.

The upper part 25 of the ATR probe 16 is provided with a fiber guide-through body 37 which is situated in a protective tube 38. A pressure screw element 39 having an adjustable screw 40 compresses a spring system 41 which forces the protective tube 38 downward against the ATR prism 17. This improves the sealing at the opening 42 left in the protective housing 16 for the prism. In particular, the springs 41 provide compensation for the longitudinal expansion of the probe and ensure that the necessary contact pressure of the prism 17 against the gasket 36 is maintained even in the event of temperature elevation.

To be able to simply separate the probe head from the rest of the measuring and optical fiber system, the upper probe part 25 has four SMA terminals 45 at which two sections of an optical fiber can be coupled to each other.

Figure 4:
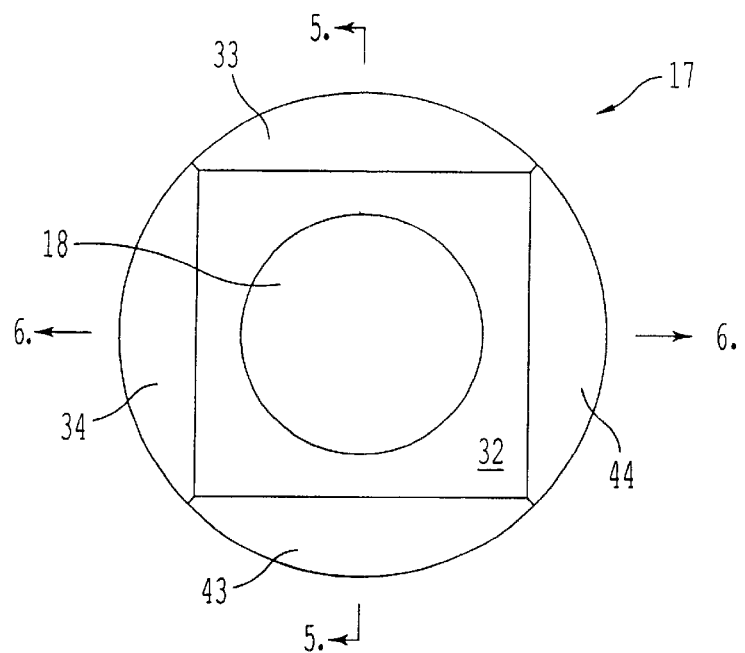
FIG. 4 shows a top view of the ATR prism according to the invention.
Figure 5:
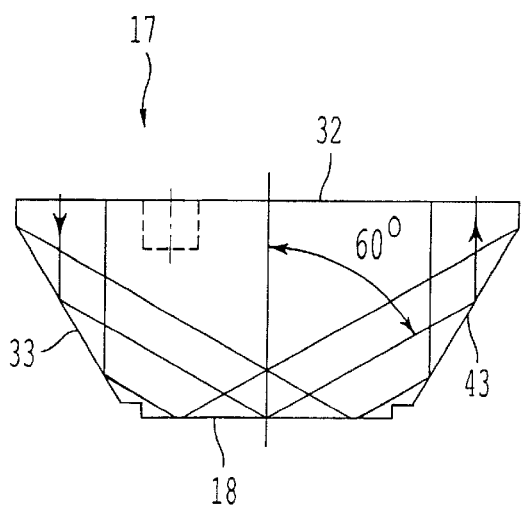
FIG. 5 shows a section along the line V—V through the prism of FIG. 4.
Figure 6:
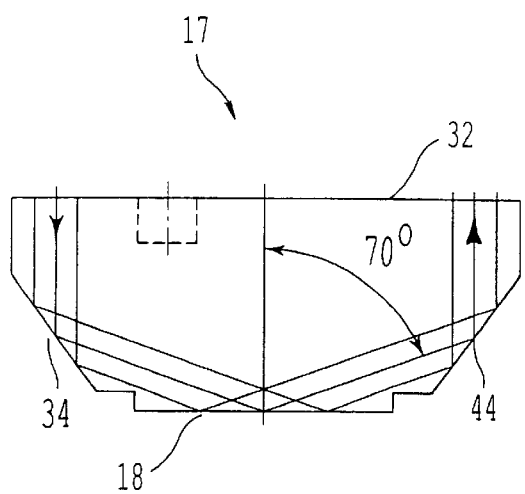
FIG. 6 shows a section along the line VI—VI through the prism of FIG. 4.

The ATR prism 17 of the invention is depicted in more detailed form in FIG. 4 in top view and in FIGS. 5 and 6 in section along the plane of incidence of the first and second beams, respectively. There are in each case two mutually opposite deflecting faces 33, 43 and 34, 44, respectively, which are offset relative to each other by an angle of 90°. When the beam passes vertically downward into the prism 17 through the entry face 32 and is to impinge upon the boundary 22 at an angle θ, the respective deflecting face must form an angle θ/2 with the perpendicular to the boundary 18. In the depicted example, the first beam has an angle of incidence of 60° and the second beam has an angle of incidence of 70°.

EXAMPLES

The measurements were carried out using a prototype of the probe according to the invention. The cylindrical probe, 26 mm in external diameter and about 320 mm in base length, was made of tantalum and could be fitted with quartz or sapphire prisms having the geometry depicted in FIGS. 4 to 6. The diameter of the circular light entry and exit face of the prisms was 22 mm, the diameter of the measuring area being about 11 mm. The first beam had an angle of incidence of 60° and the second beam had an angle of incidence of 70°. The optical fibers used were multimode glass fibers having a core diameter of 800 μm, which terminated in the upper part of the probe in F-SMA terminals. The reflected light was passed into a monolithic simultaneous multichannel spectrometer system equipped with MMS diode array spectrometer modules (256 diodes, useful region of the spectrum ranging from 300 nm to 1100 nm) from Zeiss. One module is used for measuring the intensity of the light source, while the other two modules are used for measuring the reflected light at 60° and 70°, respectively. Data acquisition was effected using a LabView® program (Version 4, National Instruments) running on a PC.

Spectra in the visible region were determined using a halogen lamp. UV spectra were determined using a deuterium discharge lamp as light source.

Example 1

Absorption Spectrum and Dispersion Curve of a Dye Solution (Copper Phthalocyanine Pigments (CuPC) in Sulfuric Acid)

CuPC pigments were dissolved in concentrated sulfuric acid ($H_2SO_4$).

Figure 7:
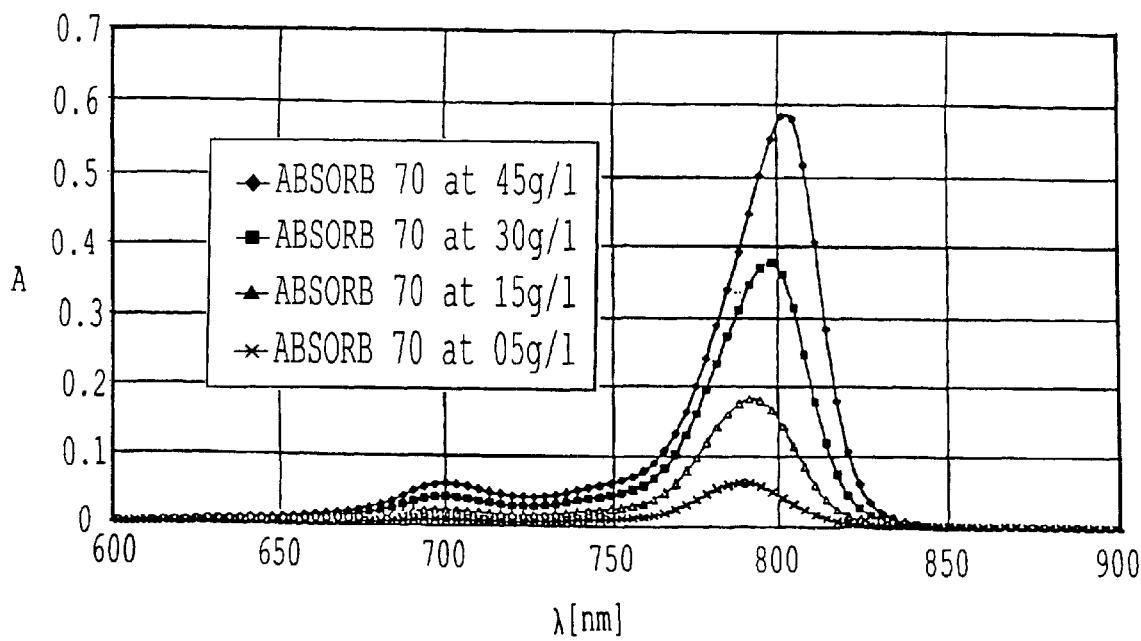
FIG. 7 shows original spectra of copper phthalocyanine solutions of varying concentrations recorded at an angle of incidence of 70° using the apparatus of the invention.
Figure 8:
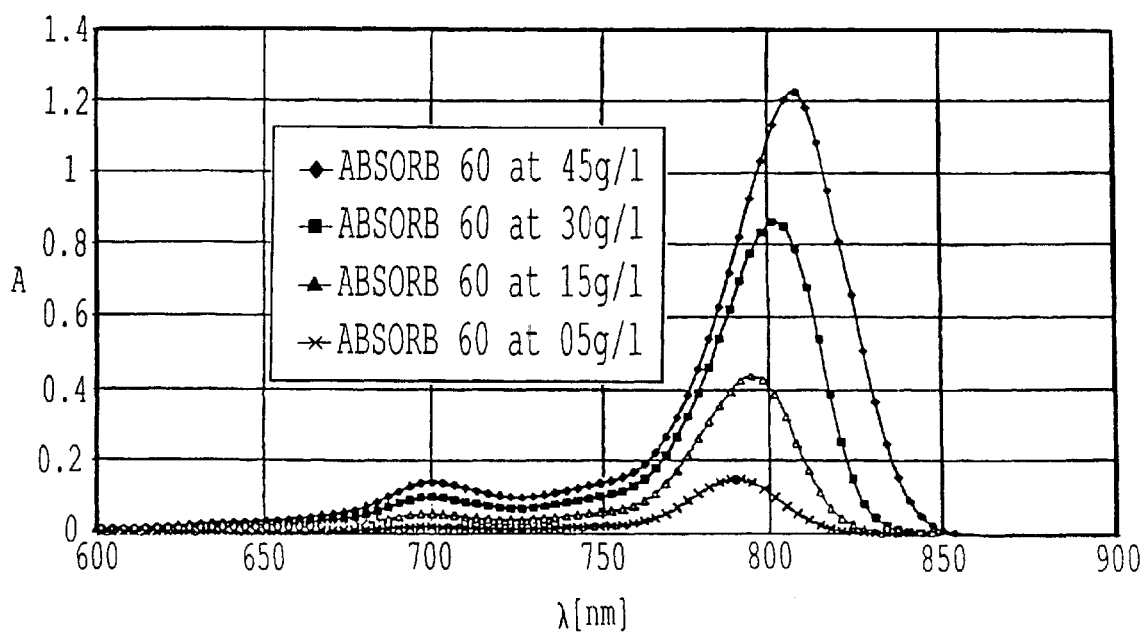
FIG. 8 shows original spectra of the solutions of FIG. 7 recorded at an angle of incidence of 60° using the apparatus of the invention.

FIGS. 7 and 8 illustrate the original spectra obtained with the apparatus of the invention at concentrations of 5, 15, 30 and 45 g/l and at angles of incidence of 70° (FIG. 7) and 60° (FIG. 8).

The first thing to notice is a bathochromic shift as the concentration of the pigments in the sulfuric acid increases. Comparing FIGS. 7 and 8 also reveals that this shift is also dependent on the angle of reflection. The spectra obtained at 60° have a larger bathochromic shift due to the larger depth of penetration of the evanescent wave at smaller angles. It is also observed that the shape of the absorption bands is not symmetrical, as would be expected for a transmission measurement. Also, the data obtained using ATR measurements are observed to depart from the Lambert-Beer law, since the absorbance A does not show any linear dependence on the concentration.

Figure 9:
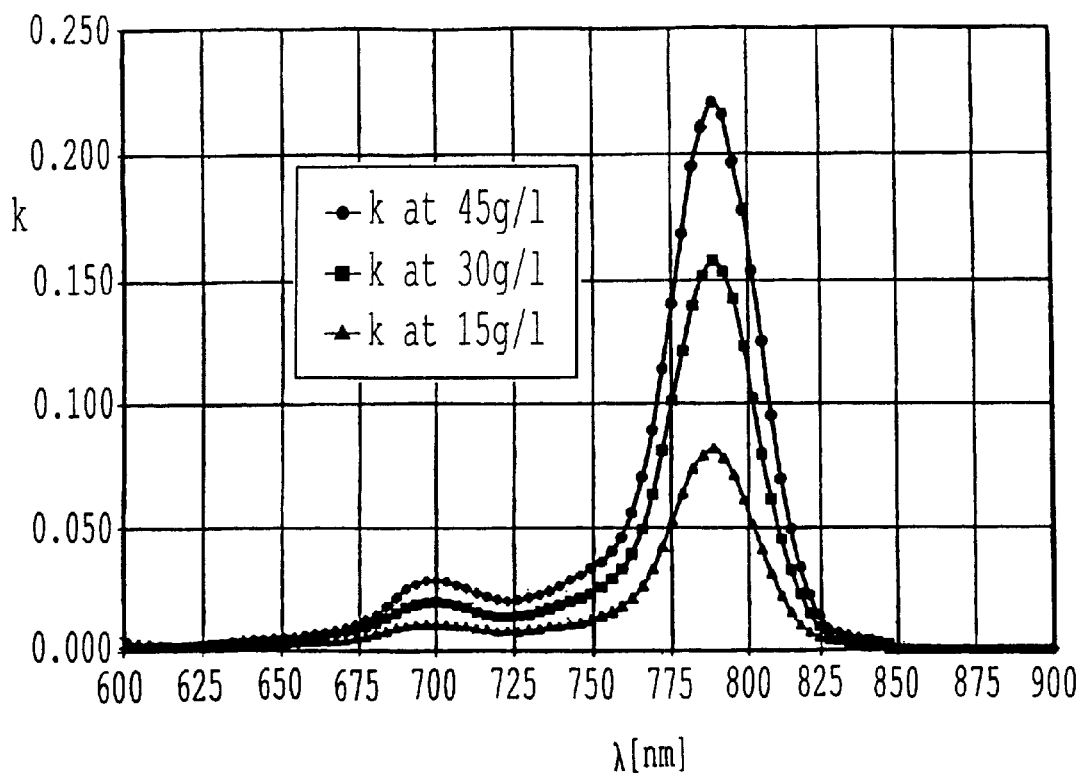
FIG. 9 shows absorption spectra calculated from the measurements of FIGS. 7 and 8 by the method of the invention.
Figure 10:
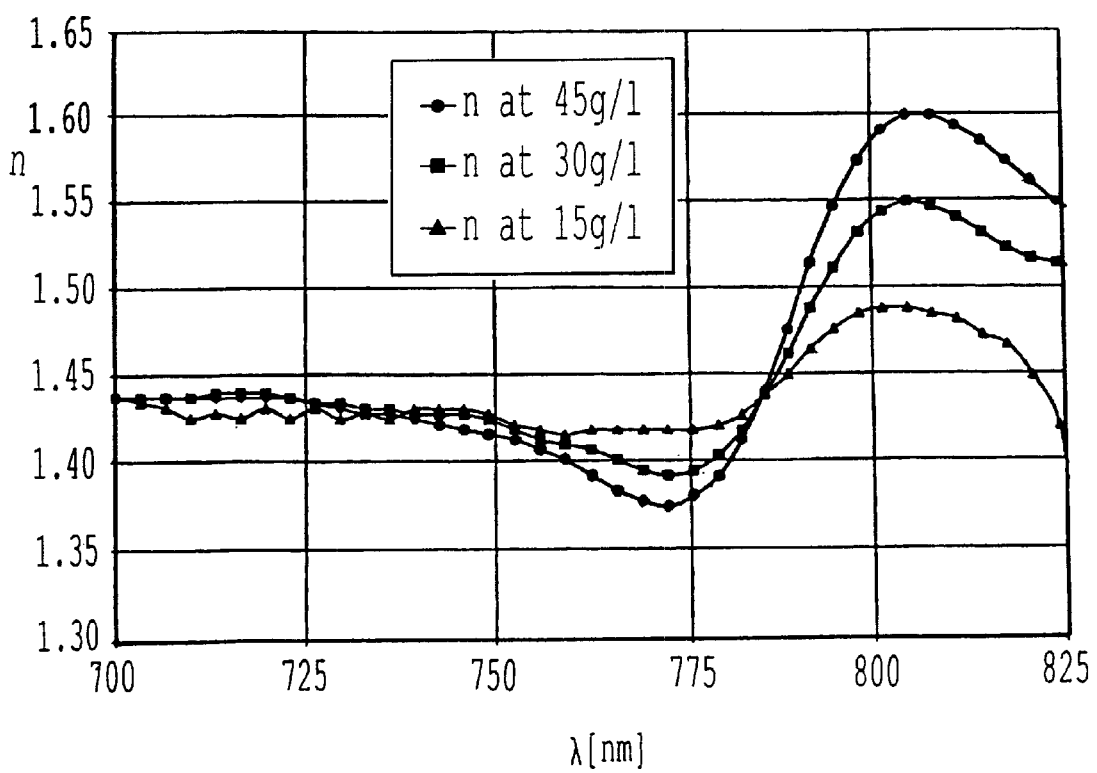
FIG. 10 shows dispersion curves calculated from the measurements of FIGS. 7 and 8 by the method of the invention.

The method of the invention was used to calculate from the measured data depicted in FIGS. 7 and 8 the absorption spectrum $k(\lambda)$ of FIG. 9 and the dispersion curve $n(\lambda)$ of FIG. 10.

It can be seen that the absorption maxima at different concentrations occur at the same wavelength. The method of the invention has corrected the bathochromic shift. Also, the absorption maximum depends essentially linearly on the concentration, so that the Lambert-Beer law is complied with as well.

The noise level of the calculated spectra is somewhat higher than that of the original measured data, but this could be corrected by employing higher computing accuracy.

We claim:

1. An apparatus for spectroscopic analysis of a fluid medium by attenuated reflection, comprising:
   first means for directing a first light beam onto a boundary of the medium to be analyzed;
   means for measuring an intensity of said first light beam reflected at the boundary;
   second means for directing a second light beam substantially simultaneously with said first light beam onto said boundary of said medium to be analyzed; and
   means for measuring an intensity of said second light beam reflected at said boundary, said first and second light beams differing in at least one of an angle of incidence upon the boundary and in polarization.

2. The apparatus of claim 1, wherein said first light beam impinges upon the boundary at a first angle $\theta_1$ and said second light beam impinges upon the boundary at a second angle $\theta_2$, which differs from the first angle $\theta_1$.

3. The apparatus of claim 2, wherein said first angle $\theta_1$ is larger than a limiting angle of total reflection at said boundary while said second angle $\theta_2$ is smaller than the limiting angle of total reflection.

4. The apparatus of claim 2, wherein said first and second angles $\theta_1$ and $\theta_2$, respectively, are both larger than a limiting angle of total reflection at said boundary.

5. The apparatus of claim 1, further comprising a probe-like cylindrical housing having a prism disposed at a free end face of said housing, said prism having at least one face wettable by the medium to be analyzed, said wettable face forming said boundary for the reflection of said first and second light beams.

6. The apparatus of claim 5, wherein said prism has an essentially frustoconical shape and comprises a light entry and exit face parallel to said boundary, a first pair of mirror-symmetrically opposite side faces which form an angle of $\theta_1/2$ with a normal to said boundary, and a second pair of mutually opposite mirror-symmetrical side faces which form an angle of $\theta_2/2$ with the normal to said boundary.

7. The apparatus of claim 6, wherein said first pair of side faces is twisted by 90° around the normal to the boundary relative to said second pair of side faces.

8. The apparatus of claim 7, wherein said prism is forced by elastic means against sealing means surrounding an opening in the end face of the cylindrical housing.

9. The apparatus of claim 1, wherein an optical path of said first light beam includes at least one of a polarizer disposed between the first means and the boundary for perpendicularly polarized light and an analyzer disposed between the boundary and the means for measuring for perpendicularly polarized light, and wherein an optical path of said second light beam includes at least one of a polarizer disposed between the second means and the boundary for parallel-polarized light and an analyzer disposed between the boundary and the means for measuring and for parallel-polarized light.

10. The apparatus of claim 1, wherein an optical path of said first and second light beams includes at least one of polarizers for perpendicularly polarized light and analyzers for perpendicularly polarized light.

11. The apparatus of claim 1, further comprising:
    first optical fibers for passing said first and second light beams onto said boundary;
    second optical fibers for passing said first and second light beams reflected at the boundary to said means for measuring the light intensities; and
    collimating means for coupling said first and second light beams in and out, respectively, said collimating means being disposed between light exit faces of said optical fibers and said boundary, and said boundary and light entry faces of said second optical fibers, respectively.

12. An apparatus for spectroscopic analysis of a fluid medium by attenuated reflection, comprising:
    a first optical fiber configured to direct a first light beam onto a boundary of the medium to be analyzed;
    a spectrometer configured to measure an intensity of said first light beam reflected at the boundary;
    a second optical fiber configured to direct a second light beam substantially simultaneously with said first light beam onto said boundary of said medium to be analyzed; and
    said spectrometer measuring an intensity of said second light beam reflected at said boundary, said first and second light beams differing in at least one of an angle of incidence upon the boundary and in polarization.

13. The apparatus of claim 12, wherein said first light beam impinges upon the boundary at a first angle $\theta_1$ and said second light beam impinges upon the boundary at a second angle $\theta_2$, which differs from the first angle $\theta_1$.

14. The apparatus of claim 13, wherein said first angle $\theta_1$ is larger than a limiting angle of total reflection at said boundary while said second angle $\theta_2$ is smaller than the limiting angle of total reflection.

15. The apparatus of claim 13, wherein said first and second angles $\theta_1$ and $\theta_2$, respectively, are both larger than a limiting angle of total reflection at said boundary.

16. The apparatus of claim 12, further comprising a probelike cylindrical housing having a prism disposed at a free end face of said housing, said prism having at least one face wettable by the medium to be analyzed, said wettable face forming said boundary for the reflection of said first and second light beams.

17. The apparatus of claim 16, wherein said prism has an essentially frustoconical shape and comprises a light entry and exit face parallel to said boundary, a first pair of mirror-symmetrically opposite side faces which form an angle of $\theta_1/2$ with a normal to said boundary, and a second pair of mutually opposite mirror-symmetrical side faces which form an angle of $\theta_2/2$ with the normal to said boundary.

18. The apparatus of claim 17, wherein said first pair of side faces is twisted by 90° around the normal to the boundary relative to said second pair of side faces.

19. The apparatus of claim 18, wherein said prism is forced by an elastic member against a seal surrounding an opening in the end face of the cylindrical housing.

20. The apparatus of claim 12, wherein an optical path of said first light beam includes at least one of a polarizer disposed between the first optical fiber and the boundary for perpendicularly polarized light and an analyzer disposed between the boundary and the spectrometer for perpendicularly polarized light, and wherein an optical path of said second light beam includes at least one of a polarizer disposed between the second optical fiber and the boundary for parallel-polarized light and an analyzer disposed between the boundary and the spectrometer and for parallel-polarized light.

21. The apparatus of claim 12, wherein an optical path of said first and second light beams includes at least one of polarizers for perpendicularly polarized light and analyzers for perpendicularly polarized light.

22. The apparatus of claim 12, further comprising:

third optical fibers configured to pass said first and second light beams onto said boundary;

fourth optical fibers configured to pass said first and second light beams reflected at the boundary to said spectrometer; and a collimator configured to couple said first and second light beams in and out, respectively, said collimator being disposed between light exit faces of said optical fibers and said boundary, and said boundary and light entry faces of said fourth optical fibers, respectively.

* * * * *